United States Patent [19]

Tryggvason et al.

[11] Patent Number: 5,354,690
[45] Date of Patent: Oct. 11, 1994

[54] IMMUNOLOGICAL METHODS FOR THE DETECTION OF THE HUMAN TYPE IV COLLAGEN α5 CHAIN

[76] Inventors: Karl Tryggvason, Fyysinkontie 8, SF-90570 Oulu; Sirkka L. Hostikka, Tapiontie 9 A 21, SF-90750 Oulu; Matti Höyhtyä, Valtatie, SF-90500 Oulu, all of Finland

[21] Appl. No.: 630,563

[22] Filed: Dec. 20, 1990

Related U.S. Application Data

[63] Continuation-in-part of Ser. No. 377,238, Jul. 7, 1989, Pat. No. 5,114,840.

[51] Int. Cl.$^5$ ............... G01N 33/53; G01N 33/569; C12Q 1/00; C07K 15/00
[52] U.S. Cl. ..................... 436/501; 436/503; 436/543; 436/547; 530/387.1; 530/387.9; 530/389.1; 530/391.1; 530/391.3; 435/7.1
[58] Field of Search ............. 435/6, 7, 7.1; 436/507, 436/501, 543, 547, 503; 530/326, 387.1, 387.4, 389.1, 381.1, 391.3

[56] References Cited

U.S. PATENT DOCUMENTS

4,554,101 11/1985 Hopp .............................. 530/324
5,082,926 1/1992 Chelberg et al. ................ 530/326

OTHER PUBLICATIONS

Identification of a distinct type IV collagen & chain with restricted kidney distribution and assignment of its gene to the locus of x-chromosome-linked Al port syndrome: Proc Natl. Acad Sci. vol. 87, pp. 1606–1610, Feb. 1990 Hostikka et al.

The Complete Primary Structure of the α2 Chain of Human Type IV Collagen and Comparison with the 21(IV) Chain, Hostikka & Trycavason J. Biol Chem., 263, No. 36 pp. 19488–19493, 1988.

Primary Examiner—Christine M. Nucker
Assistant Examiner—Chris Dubrule
Attorney, Agent, or Firm—Fay, Sharpe, Beall, Fagan, Minnich & McKee

[57] ABSTRACT

The present invention provides for a method for preparing antibodies that specifically detect the type IV collagen α5 chain that is defective in various basement membrane disorders such as in X chromosome-linked Alport's syndrome. The invention further provides for the use of such antibodies to detect the α5(IV) collagen chain in solutions and other human tissue specimens using immunological methods comprised of antibodies specific for said protein. Along this line, the invention relates to the use of the specific antibodies to examine the presence or absence of the α5(IV) collagen chain in the tissues, e.g. skin or kidneys, etc. of patients with renal failure, possibly due to Alport's syndrome.

4 Claims, No Drawings

IMMUNOLOGICAL METHODS FOR THE DETECTION OF THE HUMAN TYPE IV COLLAGEN α5 CHAIN

This is a continuation-in-part of co-pending patent application Ser. No. 377,238, filed on Jul. 7, 1989, now U.S. Pat. No. 5,114,840, issued May 19, 1992.

FIELD OF THE INVENTION

The present invention relates to immunological methods for identifying the basement membrane human type IV collagen α5 chain that is affected in various basement membrane disorders such as Alport's syndrome, an inherited kidney disease. Specifically, the methods are based on the use of antibodies prepared against peptides containing amino acid sequences that are specific for the human α5(IV) protein chain. In addition, the invention is directed to compositions comprising labeled or unlabeled synthetic peptides containing amino acid sequences that are specific for the human α5(IV) protein chain, and labeled or unlabeled antibodies specific for said peptides and the use of these compositions for diagnostic purposes.

DESCRIPTION OF THE PRIOR ART

Basement membranes are a highly specialized part of the extracellular matrix and they form thin sheets that separate the cells of organs from the fibrillar connective tissues. The basement membranes serve a number of important biological functions in the body such as in the developing embryo where they play a role in cell differentiation during the formation of organs. They are also of importance for the correct regeneration of tissues following injuries such as during post-wound reformation of skin and nerves.

Of particular importance with respect to the present invention is the filtration role of basement membranes in kidneys and blood vessels. This function is exemplified by the renal glomerular basement membrane which makes up the filter between the glomerular capillary lumen and the urinary space and hinders the passage of blood cells and large macromolecules (proteins) to the forming urine.

The basement membranes are composed of several proteins, many of which are found only in these structures. Type IV collagen is the major structural component but other specific protein components include laminin, entactin (nidogen) and proteoglycans. Additionally, the basement membranes may contain fibronectin and type VII collagen that are also present in other extracellular matrices. The differences in the molecular composition of basement membranes in different tissues is not well known but protein known as pemphigoid antigen is probably only present in the basement membranes of skin. It is currently believed that there are several other proteins that are specific for basement membranes in certain tissues.

Type IV collagen is the major structural component of basement membranes and it can provide up to 60% of the structure. As is true for collagens in general, type IV collagen molecules contain three α chains that are coiled around each other to form a long triple-helical molecule that is about 1.5 nm in diameter and about 400 nm in length. At the carboxyl terminal end, the molecule has a large globular non-collagenous domain, called NC-domain, that has a diameter of about 15 nm. Single type IV collagen molecules are linked with each other into a complex, flexible network-like structure into which the other basement membrane components are bound (Timpl, Eur. J. Biochem., 180, 487–502, 1989).

It was previously thought that the major form of type IV collagen was only composed of two kinds of chains, α1(IV) and α2(IV), with the molecular formula $[\alpha 1\text{(IV)}]_2 \alpha 2\text{(IV)}$. The applicants have determined the entire amino acid sequence of the both chains from man by applying DNA sequencing of cloned cDNA molecules (Soininen, et al., FEBS Lett., 225, 188–194, 1987; Hostikka and Tryggvason, J. Biol. Chem., 263, 19488–19493, 1988). The results showed that the α1(IV) chain contains 1,642 amino acid residues as compared with 1,676 residues in the α2(IV) chain. The carboxyl terminal NC-domain of both chains are very similar with 63% identical amino acid residues. The sequence homology of the two chains in the triple-helical region is considerably less or 49%. The existence of two other distinct type IV collagen chains, α3(IV) and α4(IV), has recently been reported, indicating that type IV collagen has several molecular compositions (Butkowski, et al., J. Biol. Chem., 262, 7874–7877, 1987; Saus, et al., J. Biol. Chem., 263, 13374–13380, 1988).

Of importance with respect to the present invention is the recent discovery by the applicants of yet another type IV collagen chain, termed α5(IV). cDNA clones that code for about 50% of the human protein sequence from the carboxyl terminal end were isolated and sequenced (Hostikka, et al., Proc. Natl. Acad. Sci. USA, 87, 1606–1610, 1990). Amino acid sequence comparison demonstrated that the α5(IV) chain is a distinct gene product which is more closely related to the α1(IV) chain than to the α2(IV) chain. In the NC-domain, the sequence identity between the α1(IV) and α5(IV) chains was shown to be as high as 83% whereas it is only 63% identical with the same region from the α2-(IV) chain. For the collagenous domain, the sequence identities were 58% and 46%, respectively. The type IV collagen collagenous domain repeat sequences (Gly-Xaa-Yaa) are characteristically interrupted by non-collagenous sequences. All the interruptions in the collagenous domain of the α5(IV) chain coincide with interruptions in the α1(IV) chain but only partially with interruptions in the α2(IV) chain.

Using cDNA probes and both somatic cell hybrids and in situ hybridization, the gene for the human type IV collagen α5 chain (COL4A5) was localized to the q22 region on the long arm of chromosome X (Hostikka, et al., Proc. Natl. Acad. Sci. USA, 87, 1606–1610, 1990). This is different from the genes (COL4A1) and (COL4A2) for the human α1(IV) and α2(IV) chains, respectively, that have both been assigned to the terminal end of the long arm of chromosome 13 (Boyd, et al., Hum. Genet., 74, 121–125, 1986; Griffin, et al., Proc. Natl. Acad. Sci. USA, 84, 512–526, 1987).

Due to their wide distribution in the body, basement membranes are frequently affected in both local and systemic diseases and, in many instances, the consequent pathological changes lead to severe clinical complications. These diseases may be both genetically determined inherited diseases that are due to gene mutations leading to an abnormal structure and function of the protein or they can be acquired, i.e. complications of diseases that do not primarily involve the basement membrane such as diabetes mellitus. Examples of inherited basement membrane diseases are: (1) Alport's (or Alport) syndrome, a hereditary nephritis caused by abnormal function of the basement membranes resulting in the passage of blood cells into urine (hematuria), eye lesions and hearing loss; and, (2) congenital nephrotic syndrome which is characterized by the extensive leak of proteins through the renal glomerular basement membrane into urine (proteinuria). Both diseases are fatal but can be treated by renal transplantation.

The applicants have recently demonstrated that the gene for the α5(IV) collagen chain is affected in certain patients with Alport's syndrome. This disease is a heterogenous group of inherited kidney diseases, that are usually linked to the X chromosome. The disease is clinically characterized by terminal renal failure of males, usually with concomitant deafness and eye lesions. Several studies have shown close linkage of the Alport's syndrome locus to the q22-24 region of the long arm on chromosome X. The major histopathological findings are patchy thickening and splitting of the renal glomerular basement membrane that forms the filtration barriers of blood during the formation of urine. This led previously to the hypothesis that type IV collagen which forms the basement membrane structural framework was defective. However, the α1(IV) and α2(IV) chains, the major type IV collagen components, could not be involved since their genes have been located to chromosome 13. As discussed above, the applicants have identified cDNA and genomic clones coding for a novel α5(IV) collagen chain and assigned its gene to the q22 region of chromosome X which is the same locus where the Alport's syndrome gene was thought to be. The α5(IV) chain was shown to be located in the normal kidney practically only in the renal glomerular basement membrane that is affected in Alport syndrome.

More importantly, the applicants have demonstrated the presence of mutations in the α5(IV) collagen gene in three different kindreds with Alport syndrome (Barker, et al., Science 248, 1224-1227, 1990; Zho, et al., Genomics, 1991, in press). One patient was shown to have a large deletion in the gene with exons 5-10 (as counted from the 3' end of the gene) completely missing. This mutation would lead to the synthesis of an α5(IV) chain that would be shorter than the normal by 240 amino acids. The amino acids missing are both from the NC-domain (47 residues) and the collagenous domain (193 residues). The altered protein would not be able to form a normal type IV collagen molecule. This, in turn, can explain the abnormal structure of the renal glomerular basement membrane and passage of blood cells into the urine of Alport's patients.

Another mutation was shown with the cDNA probes in a large kindred when the cDNA probes were hybridized with Pst I-digested DNA from affected males in a large family. The results showed the absence of a 2.2 kb Pst I fragment in affected males and the appearance of a 1.9 kb fragment not found in normal individuals. This mutation represents a point mutation in the gene, converting the TGT codon of a conserved cysteine to the TCT codon for serine (Zho et al., Genomics, 1991, in press. The combination of the (normal) 2.2 kb and 1.9 kb (abnormal) fragments was, as expected, shown to be present in all carrier mothers. Several other mutations have been demonstrated in the 25(IV) gene in other Alport patients. All mutations can be detected from blood or tissue samples using specific DNA probes designed based on the discovery of the applicants. This allows for prenatal diagnosis of individuals carrying the specific mutations.

As a result, the applicants have discovered and initially characterized cDNA and genomic clones coding for a previously unknown type IV collagen chain, α5-(IV), and have demonstrated mutations in this gene in different kindreds with Alport's syndrome. This discovery allows for the development of highly specific diagnostic methods for the mutations and for Alport's syndrome in general using both cDNA probes and immunological methods. The present invention, which is directed to a process for preparing antibodies specific to the α5(IV) collagen chain, as well as utilizing these antibodies in immunological methods specific for the detection of the α5(IV) collagen chain, is of significance for the histopathological diagnosis of basement membrane disorders such as in patients with Alport's syndrome. The methods can be applied for immunohistological examination and diagnosis of renal or other biopsy specimens from patients with renal failure of unknown causes.

SUMMARY OF THE INVENTION

The present invention provides for a method for making antibodies that specifically detect the type IV collagen α5 chain that is believed to be defective in a number of basement membrane disorders such as the X chromosome-linked Alport's syndrome. The invention further provides for the use of such antibodies to detect the α5(IV) collagen chain in solutions and other human tissue specimens using immunological methods comprised of antibodies specific for said protein. Specifically, the invention relates to the use of the specific antibodies to examine the presence or absence of the α5(IV) collagen chain in the tissues, e.g. skin or kidneys, etc. of patients with renal failure possibly due to Alport's syndrome. Furthermore, an objective of the present invention is to provide compositions, comprising both labeled and unlabeled peptides containing sequences from the α5(IV) chain antigen (either as single peptides or conjugated to a carrier molecule or matrix) or labeled or unlabeled polyclonal or monoclonal antibodies to said α5(IV) collagen chain or peptides containing sequence specific for the said polypeptide chain, and the use of the compositions for the diagnosis of basement membrane disorders, such as Alport's syndrome.

BRIEF DESCRIPTION OF THE DRAWINGS

The following is a brief description of the drawings which are presented for the purpose of illustrating the invention and not for the purpose of limiting same.

FIG. 2 (A and B) shows the coding nucleotide sequence (first line) of the cDNA clones and the derived amino acid sequence (second line) providing a part of the sequence for the human α5(IV) polypeptide chain of type IV collagen. The interruptions in the Gly-X-Y repeat sequence are shown by boxes and the cysteine residues that are all conserved in the NC-domain are encircled. The nucleotide sequence of the oligonucleotide probe coding for the Cys-Gln-Val-Cys-Met amino acid sequence is underlined.

FIG. 3 (A and B) shows alignment of the cDNA derived amino acid sequence of the novel α5(IV) polypeptide chain with corresponding region of the human α1(IV) and α2(IV) chains previously determined by the applicants.

FIG. 4 shows the alignment of a part of the sequence for the α5(IV) polypeptide chain with the corresponding reported sequences of the bovine α3(IV) and α4(IV) chains of type IV collagen.

DETAILED DESCRIPTION OF THE INVENTION

Figure 1:
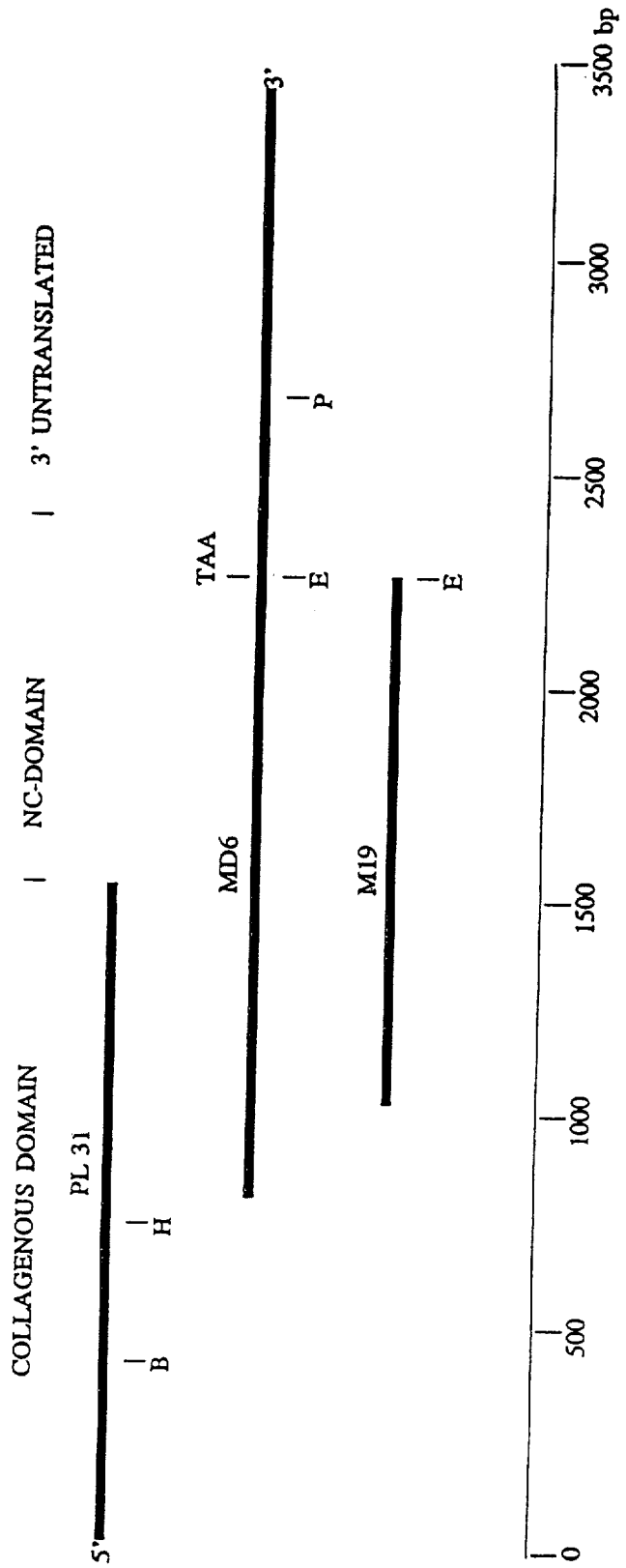
FIG. 1 is a restriction map of the three cloned cDNAs (i.e. PL31, MD5 and M19) that code for the novel α(IV) polypeptide chain of type IV collagen. A scale demonstrating the size differences in base pairs is shown below the cloned cDNAs. The regions coding for the carboxyl terminal end NC-domain of the protein as well as the part of the collagenous domain is indicated. Restriction endonuclease cleavage sites BamHI(B), EcoRI(E), HindII(H), and PstI(P) are also shown.

Methods for preparing antibodies against amino acid sequences specifically present in the human type IV collagen α5 chain, are an obligatory premise for the realization of the present invention. The applicants have, through DNA cloning techniques, discovered the novel basement membrane α5(IV) polypeptide chain and shown that is a distinct gene product (Hostikka, et al., *Proc. Natl. Acad. Sci. USA,* 87, 1606–1610, 1990; and, U.S. patent application Ser. No. 377,238, filed on Jul. 6, 1989, the parent of this continuation-in-part application). Furthermore, the applicants have demonstrated that mutations in the human α5(IV) collagen can lead to Alport's syndrome, an inherited disease mainly affecting the kidney filtration function (Barker, et al., *Science,* 240, 1224–1227, 1990; Zhou et al., Genomics, 1991, in press).

The human α5(IV) collagen chain was discovered by the isolation and sequencing of cDNA clones. The α5-(IV) collagen specific cDNA clones were isolated using as screening probes specially designed synthetic oligonucleotides containing the coding sequence for an evolutionarily conserved consensus amino acid sequence in the NC-domain present both in the human α1(IV) and α2(IV) collagen chains and in the α(IV) chain from Drosophila (Hostikka, et al., *Proc. Natl. Acad. Sci. USA,* 87, 1606–1610, 1990). Screening of cDNA libraries with this probe resulted in the isolation of a number of cDNA clones coding for the α1(IV) and α2(IV) chains, but also, in the isolation of cDNA clones coding for a previously unknown type IV collagen like chain. Four overlapping cDNA clones covered a total of 3,500 bp. A modified Northern hybridization procedure was then carried out to determine the size of mRNA coding for the protein. This was done by labeling one of the cDNA clones (MD-6) with $^{32}P$ and by hybridizing this probe to kidney RNA that had been size fractionated by agarose gel electrophoresis and transferred to nitrocellulose. This analysis demonstrated that the complete mRNA had the size of about 6,500 bp and, therefore, the cDNA clones coded for about 50% of the entire mRNA. The sizes of the mRNAs for the human α1(IV) and α2(IV) chains are also of a similar size so that the α5(IV) chain presumably has a similar size as the other two chains.

Nucleotide sequencing of the cDNA clones provided the amino acid sequence of the novel α5(IV) collagen chain. This sequence revealed that the new α5(IV) collagen resembles the previously known type IV collagen α chains in many respects. Alignment of the α5(IV) collagen sequence with those from the human α1(IV) and α2(IV) collagen chains demonstrated that the α5-(IV) collagen chain contains a complete carboxyl terminal end domain that resembles the NC-domain of the α1(IV) and α2(IV) chains. The sequence in the NC-domain was shown to be 83% identical with that of the α1(IV) but only 63% with that of the α2(IV) chain. Accordingly, the three chains, although related, are the products of three separate genes. In the region of the chain containing collagenous sequences with the typical Gly-Xaa-Yaa-repeat sequences, the α5(IV) chain showed also a higher degree of identity with the α1(IV) than the α2(IV) chain. Comparison of the sequence of α5(IV) with the short sequences reported for the α3-(IV) and α4(IV) collagen chains also showed that they are all different gene products.

The cDNA clones coding for α5(IV) collagen chain were then used to localize the gene onto a specific chromosome. See Hostikka, et al., *Proc. Natl. Acad. Sci. USA,* 87, 1606–1610, 1990, incorporated herein by reference. This was done by two different methods. First, the radio-labeled cDNA probe was hybridized to Hind III-digested DNA isolated from a panel of 36 human-mouse hybrid cell lines each of which contains several known but different human chromosomes. Analysis of the results demonstrated that all cells containing the human X chromosome hybridized with the probe. Consequently, the gene (COL4A5) for the human α5(IV) chain must be on chromosome X.

A second method provided the exact location of the COL4A5 gene on chromosome X, using in situ hybridization of individual chromosomes in dividing cells. A study on one hundred chromosomes in metaphase and prometaphase demonstrated that COL4A5 gene is located on the q22 region on the long arm of chromosome X. This finding was particularly important because the Alport's syndrome locus had been mapped to the Xq22-24 region in other studies using so-called anonymous chromosome markers (Atkin, et al. *Am. J. Hum. Genet.,* 42, 249–255, 1988; Brunner, et al., *Kidney Int.,* 34, 507–510,. 1988). Therefore, the α5(IV) gene was a clear candidate gene for the X-linked Alport's syndrome. More recent studies carried out by the applicants have demonstrated that mutations in the α5(IV) collagen gene are present in at least three different kindreds with Alport's syndrome (Barker, et al., Science, 240, 1224–1227, 1990; Zhou et al., Genomics, 1991, in press).

Having determined the amino acid sequence of about one-half of the human α5(IV) chain, it was of interest to prepare antibodies that were specific for the protein and use them to study in which tissues the novel chain is present. This posed two major problems. First of all, the intact protein could not be isolated from tissues or cells in large enough quantities to immunize animals. Secondly, it could be assumed from the high sequence homology of the α1(IV), α2(IV) and α5(IV) collagen chains that polyclonal antibodies to any of these chains would cross-react with the other two.

In order to circumvent these problems, the amino acid sequences of the three chains were searched for regions in the three chains that had low homology between them and, thus, could be used to make synthetic peptides as specific antigens for the chains. One such region in the α5(IV) collagen chain contained the sequence Ser-Asp-Met-Phe-Ser-Lys-Pro-Gln-Ser-Glu. This sequence had only 50% homology with a comparable region from the α1(IV) chain and only 20% homology with the α2(IV) chain. A peptide containing this sequence was synthesized in an automated Applied Biosystems Inc. model 430A peptide synthesizer and coupled to ovalbumin by the glutaraldehyde method (Kagen and Glick, in *Methods in Hormone Radioimmunoassay,* (Eds. Jaffe and Behrman) Academic Press, NY, pp. 328–329, 1979).

A rabbit was then immunized with subcutaneous injections of about 1 mg peptide-ovalbumin conjugate in equal volume of Freund's complete adjuvant. Boosters of the antigen conjugate together with free peptide in incomplete Freund's adjuvant were given 9 times. The specificity of the antiserum was tested by immunoblotting against different peptide-conjugated and protein isolated from cultured human fibroblasts. The total protein from confluently growing fibroblasts was extracted with an SDS-PAGE sample buffer and electrophoresed on a 6% gel after reduction with 5% $\beta$-mercaptoethanol. The size separated proteins were then transferred to a nitrocellulose filter by electroblotting. Filter strips containing the blotted protein were then incubated with the antibodies made against the $\alpha 5$(IV) chain-derived peptide. The antiserum bound to a band of the same size as the $\alpha 1$(IV) chain (185,000 daltons) as detected using a peroxidase-labeled second goat anti-rabbit antiserum. This stain could be blocked by preincubation of the antiserum with the peptide antigen demonstrating that the antibodies reacted specifically with the amino acid sequence contained in the peptide. The antibodies did not react with any protein having the size of the $\alpha 2$(IV) chain (170,000 daltons).

In order to explore whether the antibodies might react with the 50% related sequence in the similar size $\alpha 1$(IV) collagen chain, the antibodies were preincubated with a synthetic corresponding peptide-conjugate containing the sequence from the same region of that chain. This peptide, however, did not inhibit the staining of the 185,000 dalton chain by the $\alpha 5$(IV) antibodies. Therefore, it could be concluded that the antibodies specifically detect the human $\alpha 5$(IV) chain and not the $\alpha 1$(IV) chain.

The antibodies against the $\alpha 5$(IV)-derived peptide were then used to localize the $\alpha 5$(IV) chain in tissue specimens using the immunofluorosence technique. For that purpose 4-$\mu$m thick methanol fixed cryosections were prepared from human tissues obtained at autopsy. The cryosections were then immunostained according to routine procedures using fluorescein-isothiocyanate-conjugated anti-rabbit IgG and examined in Nikon Optifot microscope under UV-light. Analysis of human kidney sections gave a strong stain that was restricted in the kidney to the renal glomerulus whereas as no stain could be observed in the Bowman's capsule, proximal tubules or blood vessels. A very weak occational stain could be observed in the distal tubules.

The results provided the first solid evidence for a strictly region specific distribution of a type IV collagen component in the kidney. This finding is particularly intriguing when considering that the $\alpha 5$(IV) collagen chain that the applicants have shown to be defective in some Alport's syndrome patients is specifically located in the kidney in the glomerular basement membrane that has clear structural abnormalities. This indicates that antibodies to the $\alpha 5$(IV) chain are useful in the histological analysis and diagnosis of renal biopsies of Alport's syndrome patients. Immunohistological examination of other tissues further demonstrated restricted distribution. Thus, the $\alpha 5$(IV) chain was shown to stain the basement membrane surrounding muscle fibrils, and in skin whereas it is practically absent in the liver. In contrast, polyclonal antibodies raised against human type IV collagen isolated from placenta, presumably mainly containing $\alpha 1$(IV) and $\alpha 2$(IV) chains, gave a strong stain of all basement membranes in all tissues studied showing no region specificity.

Taken together, the amino acid sequence for the human $\alpha 5$(IV) chain that the applicants have obtained from cDNA cloning provides the possibility of making $\alpha 5$(IV) chain specific antibodies. These antibodies can be used to detect the $\alpha 5$(IV) collagen antigen in both soluble specimens and histological tissue samples using labeled second antibody methods. Since the applicants have demonstrated that the $\alpha 5$(IV) collagen gene is mutated in patients with X-linked Alport's syndrome the antibodies against the gene product is of value clinically for immunohistological studies on renal and other biopsy specimens. Recent immunohistological studies have shown abnormal staining patterns of the glomerular basement membrane in several Alport patients, thus indicating the validity of the technique.

The following examples further illustrate the specific embodiments of the present invention.

EXAMPLE 1

Synthesis of Human Type IV Collagen $\alpha 5$ Chain and $\alpha 1$ Chain Peptides A peptide with the sequence Ser-Asp-Met-Phe-Ser-Lys-Pro-Gln-Ser-Glu that is specifically found in the NC-domain of the human $\alpha 5$(IV) collagen chain and another peptide containing the sequence Ser-Glu-Met-Phe-Lys-Lys-Pro-Thr-Pro-Ser specific for the corresponding region in the human $\alpha 1$(IV) collagen chain were synthesized in an automated peptide synthesizer Applied Biosystems Inc. Model 430A according to the protocols of the manufacturer. Briefly, the first (carboxyl terminal end) amino acid of each peptide was attached to a phenylacetamidomethyl (PAM) resin to which the other amino acid residues were added as t-boc derivatives in separate cycles according to the procedures of the manufacturer. The final resin-bound decapeptide product was removed from the resin using trifluoromethanesulfonic acid (TFMSA). The soluble peptide was then precipitated twice with 4° C. diethylether at room temperature and solubilized with trifluoroacetic acid (TFA) and reprecipitated with diethylether. The precipitated peptide was then solubilized in 6M guanidine hydrochloride and partially purified by passing it over a Sephadex G-10 column. The peak fractions were lyophilized and the peptides were then further purified by preparative HPLC analysis. The sequence of each peptide was verified by sequence analysis using an automated amino acid sequencer Applied Biosystems Inc. Model 470A.

EXAMPLE 2

Preparation of Antibodies for the Human Type IV Collagen $\alpha 5$ Chain Using a Synthetic Peptide Synthetic peptide with an $\alpha 5$(IV) specific sequence was coupled to the ovalbumin carrier according to Kagen and Click (In: *Methods in Hormone Radioimmunoassay* (Eds. Jaffe and Behrman (Academic Press, New York), pp. 328–329, 1979) as follows: Twenty mg of ovalbumin (Sigma) were dissolved in 0.5 ml of a 0.4M phosphate buffer, pH 7.5. About 15 $\mu$mol (15 mg) of peptide in 1.5 ml of water was added. Then, 1.0 ml 20 mM glutaraldehyde was added dropwise during 5 min under continuous stirring and by additional stirring for 30 min at room temperature. The unreacted glutaraldehyde was blocked by addition of 0.25 ml 1 M glycine and 30 min under stirring. The excess peptide and reagent were removed by dialysis against phosphate buffered saline (PBS). The amount of peptide conjugate was expected to be that of the carrier ovalbumin used, having 20 mg in 3.25 ml which was divided into 170 μl (about 1 mg) aliquots and stored at −20° C. The incorporation of peptide to the ovalbumin-carrier was analyzed by SDS-PAGE with 0.5–1 μg samples of carrier and conjugate, and identified by the addition of molecular weight in the conjugate.

For the preparation-of antibodies, a 1 mg sample of peptide-ovalbumin conjugate (170 μl) was added to PBS in a 0.5 ml final volume and mixed to an emulsion with equal volume of Freund's complete adjuvant (Difco). The antigen was injected subcutaneously into a rabbit at several locations in the neck and back (100–200 μl/dose). A booster injection with the same amount of antigen in incomplete Freund's adjuvant was given two weeks later. Further booster injections were given at 2–4 week intervals. After the second booster, low antibody titer was detected by immunoreactions of antiserum and antigen or corresponding peptide-BSA conjugate dilution series. Thereafter, about 0.5–1 mg free peptide was added to the antigen of booster injections. The highest specific antibody titers were found after the total of eight to ten injections.

EXAMPLE 3

Immunoblotting Analysis of the Human α5(IV) Collagen Chain

One confluent 175 cm$^2$ cell culture flask of normal human skin fibroblasts was washed twice with PBS and extracted with SDS-buffer (0.0625M Tris-HCl pH 6.8 containing 2% SDS, 10% glycerol and bromphenol blue). After boiling for 3 min. and reduction with β-mercaptoethanol (final concentration 5%), the sample was run on standard SDS-PAGE using 3% stacking gel and 6% separating gel. The electrophoresed proteins were transferred to a nitrocellulose filter (φ0.45) and used for immunostaining as follows: The filter strips were washed with TBS (0.05M Tris-HCl, pH 7.6, 0.9% NaCl) and the nonspecific binding sites were blocked by 30 min. incubation in 1% BSA-TBS. The solution was removed, and antiserum (1:100 dilution) in 1% BSA-TBS was added for overnight incubation at +4° C. or two hours at room temperature. The antiserum was washed away with TBST (TBS with 0.05% Tween 20) three times 5 min and peroxidase conjugated anti-rabbit IgG (Zymed Laboratories Inc.) in TBST (1:1000 dilution) was added for one hour incubation at RT. Excess peroxidase-conjugate was removed by three times 5 min. washes with TBST. The filters were washed once with TBS for 5 min. and the substrate solution (20 mg 4-chloro-1-naphtol is solved in 1 ml ethanol, 20 ml TBS is added, the solution is warmed until it is dissolved and H$_2$O$_2$ is added to 0.01%) was added. The enzyme reaction was stopped after 10–15 min by washes with water. For antibody inhibition tests, the assay conditions were identical except that the antiserum dilution was preincubated with antigen (100 μg peptide-ovalbumin conjugate/2 ml 1:100 antiserum) or corresponding α1(IV) peptide conjugate.

The antiserum prepared against the α5(IV) specific peptide stained a band of about the same size (185,000) as the α1(IV) chain. This stain could be blocked by preincubation of the antibodies with the peptide antigen demonstrating that the antiserum specifically detected the amino acid sequence of this peptide. Since a related amino acid sequence is present in the same size α1(IV) chain, it was possible that the band detected was actually the α1(IV) and not the α5(IV) chain. In order to rule this out, the antiserum against the α5(IV) peptide was incubated with a synthetic peptide containing the related sequence (50% sequence identity) from the α1(IV) chain. However, the α1(IV) peptide did not inhibit the staining of the 185,000 dalton protein band by the α5(IV) chain. Any reaction of the α5(IV) chain antibodies with the α2(IV) chain could be ruled out by the fact a band corresponding to the size of that chain (170,000) was not stained in the experiment.

EXAMPLE 4

Immunohistological Localization of the Human α5(IV) Collagen Chain

The immunohistochemical studies were performed on 4 μm thick cryosections from an adult human kidney obtained at autopsy. The glass microscope slides were coated with 10% BSA, the cryosections were placed on the slide, air dried and stored at −20° C. . Before staining, the cryosections were fixed in methanol for 10 min. at −20° C. , and washed in TBS for 5 min. Nonspecific binding was blocked by incubation with 1% BSA-TBS for 30 min. The antiserum (1:100 dilution in 1% BSA-TBST) was allowed to react overnight at +4° C. or for 1–2 h at room temperature. Excess antiserum was removed by three 5 min washes with TBST and the tissue samples were incubated with FITC (fluorescein isothiocyanate) conjugated anti-rabbit IgG (Janssen Biochimica; 1:50 in 1% BSA-TBST) for 1–2 h at room temperature. The samples were washed three times for 5 min with TBST and once with TBS and air dried. The cryosections were then mounted with 90% glycerol in PBS and studied in a Nikon Optiphot microscope under UV-light for fluorescence.

The immunofluorescence studies with the antibodies against the human α5(IV) chain peptide showed a reaction highly restricted to the glomerular basement membrane whereas the basement membrane in the Bowman's capsule was completely negative. Furthermore, the basement membrane in the renal tubuli was negative except for some minor reaction in the distal tubuli. As in the immunoblotting experiment the immunostaining reaction could be blocked by preincubation of the antiserum with the α5(IV) peptide but not with the α1(IV) specific peptide. These results demonstrated that, in the kidney, the type IV collagen α5(IV) chain is practically a specific component of the glomerular basement membrane. In contrast, antiserum prepared against the NC-domain of type IV collagen isolated from whole human placenta containing primarily the α1(IV) and α2(IV) chains showed a strong stain of all basement membranes in the kidney including the glomerular, Bowman's capsule, vascular and tubular basement membranes.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. Antibodies which react specifically with basement membrane human type IV collagen α5 chain and not with basement membrane type IV collagen α1 and α2 chains, said antibodies being obtained by immunizing a host with a synthetic peptide consisting of the residues Ser-Asp-Met-Phe-Ser-Lys-Pro-Gln-Ser-Glu.

2. The antibodies of claim 1, wherein said synthetic peptide is coupled to a carrier protein prior to immunization.

3. A method for detecting the presence of basement human type IV collagen $\alpha 5$ chain and not basement membrane type IV collagen $\alpha 1$ and $\alpha 2$ chains in a biological sample comprising the steps of:

a) obtaining the antibodies of claim 1;
b) adding said antibodies to a biological sample; and,
c) detecting any antigen-antibody reaction in said biological sample.

4. The method of claim 3, wherein said antibodies are labelled.

* * * * *

UNITED STATES PATENT AND TRADEMARK OFFICE
CERTIFICATE OF CORRECTION

PATENT NO. : 5,354,690  
DATED : October 11, 1994  
INVENTOR(S) : Karl Tryggvason et al Page 1 of 8

It is certified that error appears in the above-indentified patent and that said Letters Patent is hereby corrected as shown below:

The title page, should be deleted to be replaced with the attached title page.
Add the Drawing Sheets, consisting of Figs.1-4, as shown on the attached pages.

Signed and Sealed this

Fifth Day of November, 1996

Attest:

BRUCE LEHMAN

*Attesting Officer*     Commissioner of Patents and Trademarks

United States Patent [19]

Tryggvason et al.

[11] Patent Number: 5,354,690
[45] Date of Patent: Oct. 11, 1994

[54] IMMUNOLOGICAL METHODS FOR THE DETECTION OF THE HUMAN TYPE IV COLLAGEN α5 CHAIN

[76] Inventors: Karl Tryggvason, Fyysinkontie 8, SF-90570 Oulu; Sirkka L. Hostikka, Tapiontie 9 A 21, SF-90750 Oulu; Matti Höyhtyä, Valtatie, SF-90500 Oulu, all of Finland

[21] Appl. No.: 630,563

[22] Filed: Dec. 20, 1990

Related U.S. Application Data

[63] Continuation-in-part of Ser. No. 377,238, Jul. 7, 1989, Pat. No. 5,114,840.

[51] Int. Cl.$^5$ ............... G01N 33/53; G01N 33/569; C12Q 1/00; C07K 15/00
[52] U.S. Cl. ............................. 436/501; 436/503; 436/543; 436/547; 530/387.1; 530/387.9; 530/389.1; 530/391.1; 530/391.3; 435/7.1
[58] Field of Search .............. 435/6, 7, 7.1; 436/507, 436/501, 543, 547, 503; 530/326, 387.1, 387.4, 389.1, 381.1, 391.3

[56] References Cited

U.S. PATENT DOCUMENTS 4,554,101 11/1985 Hopp .................. 530/324
5,082,926 1/1992 Chelberg et al. ............ 530/326

OTHER PUBLICATIONS

Identification of a distinct type IV collagen α chain with restricted kidney distribution and assignment of its gene to the locus of x-chromosome-linked Alport syndrome: Proc Natl. Acad Sci. vol. 87, pp. 1606–1610, Feb. 1990 Hostikka et al.

The Complete Primary Structure of the α2 Chain of Human Type IV Collagen and Comparison with the 21(IV) Chain, Hostikka & Trycavason J. Biol Chem., 263, No. 36 pp. 19488–19493, 1988.

*Primary Examiner*—Christine M. Nucker
*Assistant Examiner*—Chris Dubrule
*Attorney, Agent, or Firm*—Fay, Sharpe, Beall, Fagan, Minnich & McKee

[57] ABSTRACT

The present invention provides for a method for preparing antibodies that specifically detect the type IV collagen α5 chain that is defective in various basement membrane disorders such as in X chromosome-linked Alport's syndrome. The invention further provides for the use of such antibodies to detect the α5(IV) collagen chain in solutions and other human tissue specimens using immunological methods comprised of antibodies specific for said protein. Along this line, the invention relates to the use of the specific antibodies to examine the presence or absence of the α5(IV) collagen chain in the tissues, e.g. skin or kidneys, etc. of patients with renal failure, possibly due to Alport's syndrome.

4 Claims, No Drawings

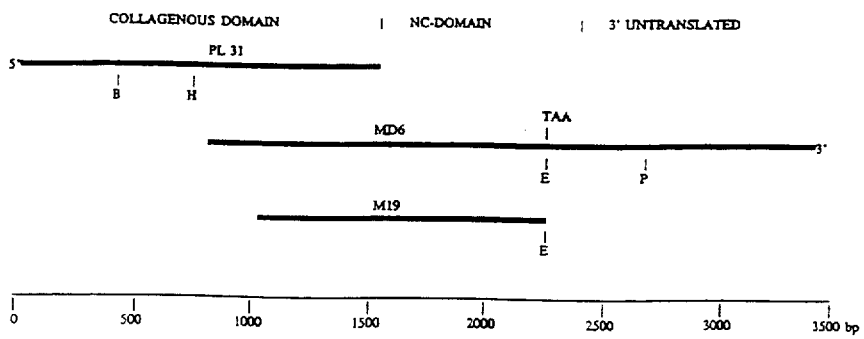

Collagenous domain ↔ NC-domain

G L X G K P G D T G P P A A G A V M R G F V F T R H Y Q    Bovine α3 (IV)

G P P G F G P G Y L S G F L L V L    Bovine α4 (IV)

G P D G L Q G P P P G P P G T S S V A H G F L T I R H S Q    Human α5 (IV)

FIGURE 4